(12) United States Patent
Centellas et al.

(10) Patent No.: US 6,599,886 B2
(45) Date of Patent: Jul. 29, 2003

(54) MACROLIDE INTERMEDIATES IN THE PREPARATION OF CLARITHROMYCIN

(75) Inventors: Victor Centellas, Cardedeu-Barcelona (ES); José Diago, Granollers-Barcelona (ES)

(73) Assignee: Biochemie S.A., Barcelona (ES)

( * ) Notice: Subject to any disclaimer, the term of this patent is extended or adjusted under 35 U.S.C. 154(b) by 0 days.

(21) Appl. No.: 09/877,778

(22) Filed: Jun. 8, 2001

(65) Prior Publication Data

US 2002/0025938 A1 Feb. 28, 2002

Related U.S. Application Data

(63) Continuation of application No. PCT/EP99/09706, filed on Dec. 9, 1999.

(30) Foreign Application Priority Data

Dec. 11, 1998 (GB) ................................ 9827355

(51) Int. Cl.⁷ ...................... A61K 31/70; C07H 17/08
(52) U.S. Cl. ............................. 514/29; 536/7.2
(58) Field of Search .................... 536/7.2, 18.6; 514/29

(56) References Cited

U.S. PATENT DOCUMENTS 5,844,105 A * 12/1998 Liu et al. .................. 536/18.5

FOREIGN PATENT DOCUMENTS

| EP | 180 415 | 5/1986 |
|----|---------|--------|
| EP | 272 110 | 6/1988 |
| WO | WO 98/04573 | 2/1998 |
| WO | WO 98/04574 | 2/1998 |
| WO | WO 98/31699 | 7/1998 |
| WO | WO 98/41532 | 9/1998 |

OTHER PUBLICATIONS

Iwasaki H. et al., Acta Crystalgraphica Section C, Crystal Structure Communications, vol. C49, No. 5, pp. 1227–1230 (1993) XP 002043675.

* cited by examiner

*Primary Examiner*—Elli Peselev
(74) *Attorney, Agent, or Firm*—Hesna J. Pfeiffer

(57) ABSTRACT

The present invention relates to a process for the production of clarithromycin from an aqueous medium in anhydrous form and in the form of a hydrate.

8 Claims, No Drawings

MACROLIDE INTERMEDIATES IN THE PREPARATION OF CLARITHROMYCIN

This is a continuation of International Application No. PCT EP 99/09706, filed Dec. 9, 1999, the contents of which are incorporated herein by reference.

The present invention relates to clarithromycin (see Merck Index, 12$^{th}$ edition (1996), page 2404) of formula I, a well known and useful antibacterial agent:

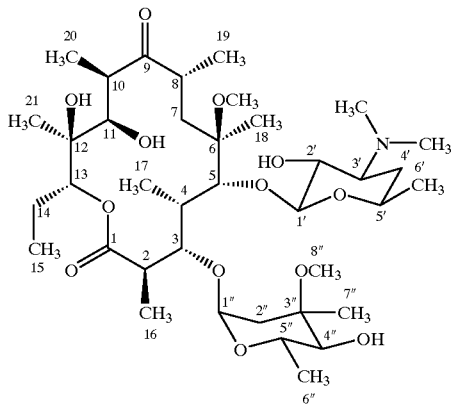

I

A compound of formula I may be prepared in anhydrous form by known methods which typically require recrystallization of the crude product using various organic solvents or mixtures thereof for purification. A purified compound of formula I may be obtained in anhydrous form, e.g. with a water content of lower than 2%, e.g. clarithromycin crystal form II.

It has now surprisingly been found that a compound of formula I in pure form may be obtained from an aqueous medium in anhydrous form and in the form of a hydrate.

Thus in one aspect the invention provides a process for the production of a compound of formula I which comprises the steps of
  (i) producing a solution of compound of formula I in the form of a salt in a solvent,
  (ii) adjusting the pH, and
  (iii) isolating a compound of formula I,
characterised in that the solvent in step (i) is an aqueous solvent medium which is selected from water or a mixture of water and organic solvent.

Advantages of the process include:
  (i) elimination of large amounts of organic solvents according to the present invention in comparison with prior art processes, and
  (ii) reducing the content of organic solvent in a compound of formula I, and
  (iii) the process according to the present invention may be carried out on technical sale.

A process according to the present invention may be carried out as follows:

A compound of formula I, e.g. in crude form, as obtained in a production process, in the form of a salt, e.g. a salt with an acid, e.g. an acid as described below, may be dissolved in an aqueous solvent medium, or a compound of formula I in free form may be dissolved by addition of an acid, e.g. an organic acid, for example formic acid or acetic acid, or an inorganic acid, for example a hydrochloric, hydrobromic, nitric or sulphuric acid, preferably hydrochloric acid or sulphuric acid, to form in situ a salt with the dimethylamino group in 3'position of the sugar radical attached to the ring system in position 5. An aqueous solvent medium includes water or a mixture of water with one or more organic solvents, for example water miscible and water immiscible organic solvents, such as alcohols, e.g. methanol, ethanol or isopropanol; ketones such as acetone or methyl isobutyl ketone; alkyl esters such as of formic or acetic acid, e.g. methyl acetate, ethyl acetate, isopropyl acetate and butyl acetate; aromatic hydrocarbons such as toluene or xylenes, ethers such as tetrahydrofuran or methyl t-butyl ether; chlorinated hydrocarbons such as methylene chloride and amides such as monoalkyl and dialkyl amides, e.g. N-methylformamide, dimethylacetamide and dimethylformamide, preferably water or a mixture of water with alcohols, ketones and aromatic hydrocarbons, e.g. water or water containing 0.5 to 20% v/v, such as 1 to 15% v/v, organic solvent. An aqueous medium may, beside water, comprise one or more individual organic solvents, e.g. as described above. Appropriate reaction conditions for the production of a compound of formula I in the form of a salt according to the present invention may include, e.g.
  (i) a temperature range of about −15° C. up to the reflux temperature of the solvent system present, such as from −10° C. to 50° C., e.g. from −5° C. to 40° C.;
  (ii) an appropriate pressure, e.g. atmospheric pressure, and a pressure which is above or below atmospheric pressure; and
  (iii) appropriate dilution, e.g. a dilution range between 1 g and 500 g of a starting compound of the formula I per liter of aqueous medium.

A resulting solution of a compound of formula I in the form of a salt in an aqueous solvent medium may be filtered, e.g. after charcoal treatment, to remove impurities and the pH of a filtered solution obtained may be adjusted to an appropiate value, e.g. by addition of a base. Suitable bases include, for example, an inorganic base, such as, for example ammonia or an alkali, e.g. sodium, potassium; earth alkali, e.g. calcium, magnesium; and ammonium; hydroxide, carbonate, bicarbonate; and an organic base, such as an amine, e.g. an alkyl amine, or a mixture of individual bases, e.g. as described above. A base may be preferably a hydroxide, e.g. sodium or ammonia; preferably in aqueous solution. The term "appropriate pH" includes a pH range wherein the compound of formula I is present in solution or suspension in the form of a free base. An appropriate pH value includes, e.g. about 7.0 to 10.0, such as 7.5 to 9.5, for example 8.0 to 9.0. A compound of formula I may precipitate and may be isolated, e.g. by a method as conventional, e.g. by centrifugation or filtration, and dried, for example at a temperature of about 30 to 100° C. to provide a compound of formula I in pure form, e.g. having a low organic solvent content.

A compound of formula I may be obtained in the form of a hydrate or in anhydrous form depending on the reaction conditions, drying conditions, and on the type and amount of solvent used:
  (A) If in the production of a compound of formula I exclusively water is used as the aqueous medium, a compound of formula I in the form of a stable hydrate may be obtained having
    (I) a water content of about 9 to 12%, such as about 9.5 to 11.5%, e.g. 10.0 to 11.0%, e.g. 10.7 to 10.8%, if the process temperature is a temperature higher than 24° C., such as 25 to 50° C., e.g. 30 to 40° C. or
    (II) a water content of 5.5 to 8%, e.g. 6 to 7%, if the process temperature is lower than 25° C., such as 15 to 24° C., e.g. 20 to 24° C.

A compound of formula I in the form of a hydrate having a water content of 9 to 12% may be crystalline. The differential scanning calorimetry of a compound of formula I in the form of a hydrate having a water content of 9 to 12% may show at a heating rate of 10° C./min an endotherm, i.e. loss of water, between room temperature and 90° C.; an exothermic transition, i.e. related to a phase transition, at about 127 to 140° C.; and an endothermic peak at 224.6° C., i.e. because of melting of a compound of formula I in the form of a hydrate having a water content of 9 to 12%. Thermal gravimetric analysis at a heating rate of 5° C./minute may show a 9.2% weight loss between room temperature and 85° C. X-ray powder diffraction patterns of a compound of formula I in the form of a hydrate having a water content of 9 to 12% are given in Table 1 and more detailed in Table 2.

TABLE 1

| d(A) | I/I$_0$ |
| --- | --- |
| 8.8 | 62 |
| 8.4 | 37 |
| 7.2 | 34 |
| 6.5 | 31 |
| 6.3 | 100 |
| 5.9 | 42 |

TABLE 2

| d(A) | I/I$_0$ |
| --- | --- |
| 9.3 | 20 |
| 8.8 | 62 |
| 8.4 | 37 |
| 7.2 | 34 |
| 6.5 | 31 |
| 6.3 | 100 |
| 5.9 | 42 |
| 5.4 | 22 |
| 4.9 | 25 |
| 4.8 | 29 |
| 4.2 | 25 |
| 4.1 | 23 |

In Tables 1 and 2 "d" denotes the interplanar spacing; I/I$_0$ denotes the relative intensity and A denotes Angstrom.

A compound of formula I in the form of a hydrate having a water content of 5.5 to 8% may be crystalline. X-ray powder diffraction patterns of a compound of formula I in the form of a hydrate having a water content of 5.5 to 8% are given in Table 3 and more detailed in Table 4.

TABLE 3

| d(A) | I/I$_0$ |
| --- | --- |
| 8.2 | 30 |
| 7.5 | 100 |
| 4.7 | 35 |

TABLE 4

| d(A) | I/I$_0$ |
| --- | --- |
| 11.5 | 20 |
| 8.2 | 30 |
| 7.5 | 100 |
| 5.7 | 27 |
| 4.8 | 20 |
| 4.7 | 35 |

In Tables 3 and 4 "d" denotes the interplanar spacing; I/I$_0$ denotes the relative intensity and A denotes Angstrom.

Thus in another aspect the present invention provides a compound of formula I in the form of a hydrate having a water content of 9 to 12%, for example in crystalline form, e.g. having a X-ray powder diffraction pattern of Table 1, or e.g. Table 2.

In another aspect the present invention provides a compound of formula I in the form of a hydrate having a water content of 5.5 to 8.0%, for example in crystalline form, e.g. having a X-ray powder diffraction pattern of Table 3, or e.g. Table 4.

(B) If in the production of a compound of formula I a mixture of water and an alcohol, e.g. methanol, ethanol or isopropanol, in a ratio of 6:1 to 15:1, such as e.g. 8:1 to 10:1, e.g. 9:1 is used as the aqueous medium, a compound of formula I in the form of a stable hydrate may be obtained having a water content of 5.5 to 8%, such as about 5.5 to 7.5%, e.g. 6 to 7%. An isolated compound of formula I may be dried (I) at a temperature below 70° C. to obtain a compound of formula I in the form of a hydrate having a water content below 5.5 to 8%, but may recover within several hours under normal environmental conditions to a water content of 5.5 to 8%, or (II) at a temperature higher than 70° C., e.g. at 110° C. for several hours, e.g. 20 or more hours, to obtain a compound of formula I in anhydrous form, e.g. having a water content below 2%, which may be considered as an isomorphic desolvate of the hydrated product.

The differential scanning calorimetry of an isolated compound of the formula I having a water content of 5.5 to 8% may show at a heating rate of 10° C./minute an endotherm, i.e. loss of water, between room temperature and 90° C., an exothermic transition between about 140 to 175° C., and an endothermic peak at 222.9° C., i.e. the melting of the product. A compound of formula I in the form of a hydrate having a water content of 5 to 8% as well as a compound of formula I in anhydrous form may be crystalline, e.g. having a X-ray powder diffraction patterns of Table 5 and more detailed of Table 6.

TABLE 5

| d(A) | I/I$_0$ |
| --- | --- |
| 9.5 | 66 |
| 7.4 | 100 |
| 4.84 | 41 |
| 4.80 | 37 |
| 4.7 | 37 |
| 4.6 | 45 |

TABLE 6

| d(A) | I/I$_0$ |
| --- | --- |
| 9.5 | 66 |
| 8.1 | 29 |
| 7.9 | 27 |
| 7.4 | 100 |
| 5.9 | 29 |
| 5.6 | 25 |
| 5.50 | 24 |
| 5.47 | 26 |
| 4.84 | 42 |
| 4.80 | 37 |
| 4.7 | 37 |
| 4.6 | 45 |
| 4.4 | 22 |
| 3.90 | 23 |
| 3.88 | 22 |

In Tables 5 and 6 "d" denotes the interplanar spacing; I/I$_0$ denotes the relative Intensity and A denotes Angstrom.

In another aspect the present invention provides a compound of formula I in the form of a hydrate having a water content of 5.5 to 8.0%, for example in crystalline form, e.g. having a X-ray powder diffraction pattern of Table 5, or e.g. Table 6.

Known anhydrous 6-O-methyl erythromycin A, e.g. currently on the market, shows a X-ray powder diffraction pattern as described in Table 7 below (crystalline form II of clarithromycin).

In yet another aspect the present invention provides a compound of formula I in anhydrous form, e.g. having a water content below 2%, for example in crystalline form, having a X-ray powder diffraction pattern of Table 5, or e.g. Table 6.

(C) If in the production of a compound of formula I a mixture of water containing very small amounts of a ketone, e.g. acetone is used as the aqueous medium (I) in a v/v ratio water:ketone of, e.g. about 25:1, a compound of formula I in anhydrous form e.g. having a water content of less than 2%, may be obtained, for example in crystalline form, e.g. having a X-ray powder diffraction pattern of Table 5. An isolated compound of formula I in anhydrous form may be dried at a temperature below 70° C. to obtain a pure compound of formula I in anhydrous form having a X-ray powder diffraction pattern of Table 5;

(II) in a v/v ratio water:ketone of, e.g. about 125:2, a mixture of a compound of formula I in the form of a hydrate having a X-ray powder diffraction pattern of Table 1 and a compound of formula I in anhydrous form having a X-ray powder diffraction pattern of Table 7 may be obtained. Upon drying of this mixture at a temperature above 70° C. a pure compound of formula I in anhydrous form having a X-ray powder diffraction pattern of Table 7 (crystalline form II of clarithromycin) may be obtained.

TABLE 7

| d(A) | I/I$_0$ |
|------|---------|
| 10.4 | 54 |
| 9.4 | 100 |
| 8.2 | 85 |
| 7.8 | 83 |
| 5.9 | 72 |
| 5.4 | 42 |
| 5.3 | 63 |
| 5.1 | 69 |
| 4.9 | 39 |
| 4.7 | 80 |

In Table 7 "d" denotes the interplanar spacing; I/I$_0$ denotes the relative intensity and A denotes Angstrom.

(D) If in the production of a compound of formula I a mixture of water containing very small amounts of an organic solvent, e.g. ethylacetate or toluene, is used as the aqueous medium in a v/v ratio water:organic solvent of, e.g. about 25:1, or less, for example, e.g. about 125:2, a compound of formula I in anhydrous form e.g. having a water content of less than 2%, may be obtained, for example in crystalline form, e.g. having a X-ray powder diffraction pattern of Table 7. An isolated compound of formula I in anhydrous form may be dried at a temperature below 70° C. to obtain a pure compound of formula I in anhydrous form having a X-ray powder diffraction pattern of Table 7 (crystalline form II of clarithromycin).

(E) In the production of a compound of formula I In the form of a stable hydrate, e.g. obtained under the process conditions described under (A), a compound of formula I in anhydrous form, e.g. having a water content lower than 2.0% may be obtained after drying for several hours at temperatures higher than 70° C., such as higher than 90° C., e.g. at about 100 to 110° C. A compound of formula I in anhydrous form, e.g. having a water content lower than 2.0% may be stable, non-hygroscopic and crystalline, e.g. having a X-ray powder diffraction pattern of Table 5, and may show similar characteristics to known anhydrous clarithromycins (crystalline form II of clarithromycin). Appropriate drying conditions may include an appropriate pressure, e.g. atmospheric pressure, and a pressure which is below atmospheric pressure, e.g. under vacuum.

A ciarithromycin in each of the novel forms according to the present invention, e.g. a compound of formula I, in the form of a hydrate, e.g. having a X-ray powder diffraction pattern described in any of Tables 1 to 6, and a compound of formula I in anhydrous form having a X-ray powder diffraction pattern described in Tables 5 or 6 shows similar activity characteristics to the known form of clarithromycin currently on the market. Clarithromycin in the form of a novel hydrate or in novel anhydrous form of the present invention may thus be used in the same indications and in the same dosages as known clarithromycin forms, e.g. forms currently on the market.

In another aspect the present invention provides a pharmaceutical composition comprising a therapeutically effective amount of a compound of formula I in the form of a stable hydrate, e.g. having a water content of approximately 5.5 to 12%, or in anhydrous form, having a X-ray powder diffraction pattern of Table 5, in combination with a pharmaceutically acceptable carrier.

In yet a another aspect the present invention provides a method of treating bacterial infections in a host mammal in need of such treatment comprising administering to the mammal a therapeutically effective amount of a compound of formula I in the form of a hydrate or in anhydrous form, preferably in combination with a pharmaceutically acceptable carrier.

The following examples may illustrate the invention without limiting its scope. All temperatures are given in degree Celsius and are uncorrected.

EXAMPLE 1

5.0 g of crude clarithromycin, as obtained in a production process, e.g. as conventional, are suspended in 300 ml of water at 25 to 30° C. 7 ml of 1N hydrochloric acid is added to adjust the pH to about 2.5 to 3.0 resulting in a slightly turbid solution of clarithromycin hydrochloride. The solution is filtered, and to the resulting clear solution an aqueous sodium hydroxide solution is added to adjust the pH to about 8.5. Clarithromycin in the form of a free base precipitates and the resulting suspension is filtered. Pure crystalline clarithromycin in the form of a stable hydrate is obtained and dried at 65° C.

Yield: 4.85 g

IR (KBr): 3467, 2973, 2937, 1735, 1460, 1378, 1344, 1168, 1124, 1110, 1082, 1053, 1037, 1011 cm-1

DSC: endoterm between room temperature and 90° C. (loss of water), exotherm at 127–140° C. (phase transition), endothermic peak at 224.6° C. (melting)

Thermal gravimetric analysis: 9.2% weight loss between room temperature and 85° C.

Water content (Karl Fisher): 10.78%

X-ray powder diffraction pattern as described in Tables 1 and 2.

1.0 g of that pure crystalline clarithromycin in the form of a stable hydrate are dried at 100° C. for 22 hours. Clarithromycin in anhydrous form having a water content of 1.60% (Karl Fischer method) and a X-ray powder diffraction pattern as described in Table 5 is obtained.

Yield: 0.9 g

IR (KBr): 3488, 3469, 2978, 2967, 2940, 2907, 1733, 1692, 1459, 1378, 1365, 1354, 1321, 1171, 1121, 1108, 1087, 1069, 1051, 1034, 1011, 1001, 976, 962 cm-1

EXAMPLE 2

Example 1 is repeated but using 2.5 g instead of 5.0 g of crude clarithromycin and a mixture of 135 ml of water and 15 ml of ethanol instead of 300 ml of water. Pure crystalline clarithromycin is obtained and dried at 65° C.

Yield: 2.52 g

IR (KBr): 3535, 3455, 2972, 2941, 1735, 1461, 1376, 1347, 1334, 1168, 1128, 1109, 1073, 1054, 1034, 1015, 984 cm-1

Water content (Karl Fisher): 6.88%

X-ray powder diffraction pattern as described in Tables 5 and 6.

1.0 g of that pure crystalline clarithromycin in the form of a stable hydrate are dried at 100° C. for 22 hours to obtain clarithromycin in anhydrous form having a water content of 1.83% (Karl Fischer method).

IR (KBr): 3466, 2977, 2940, 1735, 1691, 1461, 1376, 1350, 1334, 1283, 1169, 1126, 1110, 1072, 1053, 1034, 1014, 984, 959 cm-1

X-ray powder diffraction pattern as described in Tables 5 and 6.

EXAMPLE 3

Reaction conditions as described in example 2, but using 15 ml of methanol instead of ethanol. 2.42 g of pure crystalline clarithromycin in the form of a stable hydrate are obtained.

IR (KBr): 3535, 3455, 2972, 2941, 1735, 1461, 1376, 1347, 1334, 1168, 1128, 1109, 1073, 1054, 1034, 1015, 984 cm-1

Water content (Karl Fisher): 6.84%

X-ray powder diffraction pattern as described in Tables 5 and 6.

1.1 g of that pure crystalline clarithromycin in the form of a stable hydrate are dried at 100° C. for 22 hours to obtain 1.0 9 of clarithromycin in anhydrous form having a water content of 1.43% (Karl Fischer method).

IR (KBr): 3466, 2977, 2940, 1735, 1691, 1461, 1376, 1350, 1334, 1283, 1169, 1126, 1110, 1072, 1053, 1034, 1014, 984, 959 cm-1. X-ray powder diffraction pattern as described in Tables 5 and 6.

EXAMPLE 4

Reaction conditions as described in example 2, but using 15 ml of isopropanol instead of ethanol. 2.42 g of pure crystalline clarithromycin in the form of a stable hydrate are obtained.

IR (KBr): 3535, 3455, 2972, 2941, 1735, 1461, 1376, 1347, 1334, 1168, 1128, 1109, 1073, 1054, 1034, 1015, 984 cm-1

Water content (Karl Fisher): 6.84%

X-ray powder diffraction pattern as described in Tables 5 and 6.

0.99 g of that pure crystalline clarithromycin in the form of a stable hydrate are dried at 100° C. for 22 hours to obtain 0.96 g of clarithromycin in anhydrous form having a water content of 1.99% (Karl Fischer method).

IR (KBr): 3466, 2977, 2940, 1735, 1691, 1461, 1376, 1350, 1334, 1283, 1169, 1126, 1110, 1072, 1053, 1034, 1014, 984, 959 cm-1. X-ray powder diffraction pattern as described in Tables 5 and 6.

EXAMPLE 5

Example 2 is repeated but suspending 2.5 g of crude clarithromycin in a mixture of 125 ml of water and 5 ml of acetone instead of 135 ml of water and 15 ml of ethanol. Pure crystalline clarithromycin in anhydrous form is obtained and dried at 65° C.

Yield: 2.2 g

IR (KBr): 3529, 3456, 2975, 2940, 1735, 1690, 1461, 1376, 1349, 1334, 1283, 1168, 1127, 1110, 1082, 1073, 1054, 1034, 1015, 984 cm-1.

Water content (Karl Fisher): 1.31%

X-ray powder diffraction pattern as described in Tables 5 and 6.

EXAMPLE 6

Reaction conditions as described in example 5, but using 5 ml of ethylacetate instead of acetone. 2.32 g of pure crystalline clarithromycin in anhydrous form are obtained.

IR (KBr): 3529, 3456, 2975, 2940, 1735, 1690, 1461, 1376, 1349, 1334, 1283, 1168, 1127, 1110, 1082, 1073, 1054, 1034, 1015, 984 cm-1.

Water content (Karl Fisher): 1.17%

X-ray powder diffraction pattern as described in Table 7.

EXAMPLE 7

Reaction conditions as described in example 5, but using 5 ml of toluene instead of acetone. 2.17 g of pure crystalline clarithromycin in anhydrous form are obtained.

IR (KBr): 3529, 3456, 2975, 2940, 1735, 1690, 1461, 1376, 1349, 1334, 1283, 1168, 1127, 1110, 1082, 1073, 1054, 1034, 1015, 984 cm-1

Water content (Karl Fisher): 1.09%

X-ray powder diffraction pattern as described in Table 7.

EXAMPLE 8

Reaction conditions as described in example 5, but using 2 ml of toluene instead of 5 ml of acetone. 2.2 g of pure crystalline clarithromycin in anhydrous form are obtained.

IR (KBr): 3529, 3456, 2975, 2940, 1735, 1690, 1461, 1376, 1349, 1334, 1283, 1168, 1127, 1110, 1082, 1073, 1054, 1034, 1015, 984 cm-1

Water content (Karl Fischer): 0.95%

X-ray powder diffraction pattern as described in Table 7.

EXAMPLE 9

Example 2 is repeated but suspending 2.5 g of crude clarithromycin in a mixture of 150 ml of water and 2 ml of acetone instead of 135 ml of water and 15 ml of ethanol. Pure crystalline clarithromycin in the form of a hydrate, having a water content of 4.35% by Karl Fischer, is obtained and dried at 65° C.

Yield: 2.2 g

The X-ray powder analysis shows a mixture of the hydrate having the X-ray powder diffraction pattern of Tables 1 and 2 and the anhydrous form with the X-ray powder diffraction of Table 7.

1.13 g of that pure crystalline clarithromycin in the form of a stable hydrate are dried at 100° C. for 20 hours 1.0 g of clarithromycin in anhydrous form are obtained having a water content of 1.99% (Karl Fischer method) and a x-ray powder diffraction pattern of Table 7.

What is claimed is:
1. The compound having the formula

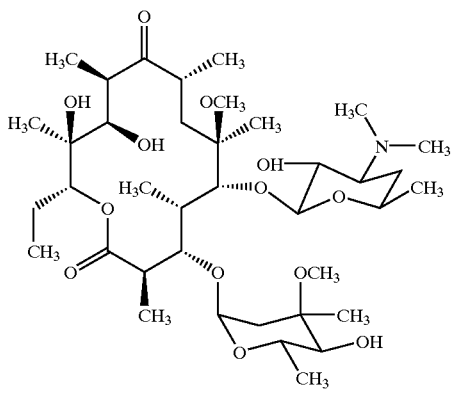

which is a stable hydrate having a water content of 9 to 12% and an X-ray diffraction pattern of the following:

| d(A) | I/I$_0$ |
|---|---|
| 8.8 | 62 |
| 8.4 | 37 |
| 7.2 | 34 |
| 6.5 | 31 |
| 6.3 | 100 |
| 5.9 | 42. |

2. The compound having the formula

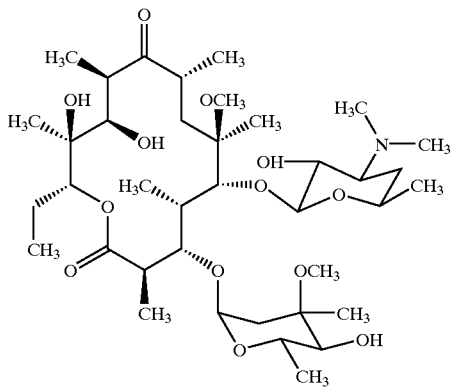

which is a stable hydrate having a water content of 5.5 to 8% and an X-ray diffraction pattern of the following:

| d(A) | I/I$_0$ |
|---|---|
| 8.2 | 30 |
| 7.5 | 100 |
| 4.7 | 35. |

3. A pharmaceutical composition comprising the compound of claim 1 in combination with a pharmaceutically carrier.

4. A pharmaceutical composition comprising the compound of claim 2 in combination with a pharmaceutically carrier.

5. The compound having the formula

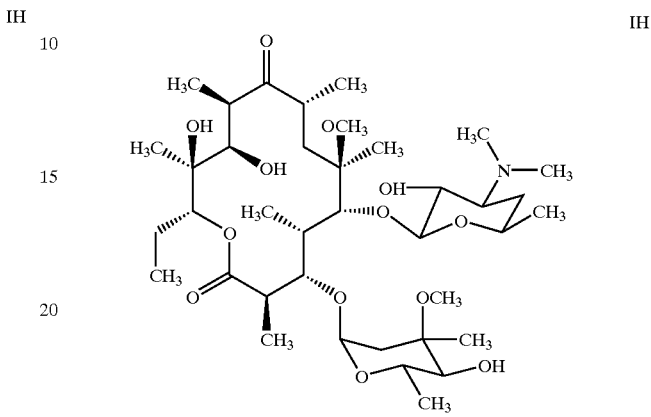

having an X-ray diffraction pattern of the following:

| d(A) | I/I$_0$ |
|---|---|
| 9.5 | 66 |
| 7.4 | 100 |
| 4.84 | 41 |
| 4.80 | 37 |
| 4.7 | 37 |
| 4.6 | 45. |

6. A pharmaceutical composition comprising the compound of claim 5 in combination with a pharmaceutically carrier.

7. The compound having the formula

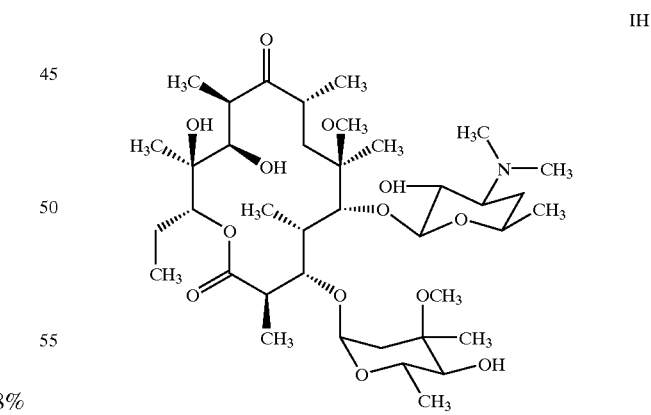

and an X-ray diffraction pattern of the following:

| d(A) | I/I$_0$ |
|---|---|
| 9.5 | 66 |
| 7.4 | 100 |

-continued

| d(A) | I/I₀ |
|---|---|
| 4.84 | 41 |
| 4.80 | 37 |
| 4.7 | 37 |
| 4.6 | 45 | in anhydrous form.

8. A pharmaceutical composition comprising the compound of claim 7 in combination with a pharmaceutically carrier.

* * * * *